US006270791B1

(12) United States Patent
Van Dyke et al.

(10) Patent No.: US 6,270,791 B1
(45) Date of Patent: Aug. 7, 2001

(54) SOLUBLE KERATIN PEPTIDE

(75) Inventors: Mark E. Van Dyke, Fair Oaks Ranch; Cheryl R. Blanchard; Scott F. Timmons, both of San Antonio; Arlene J. Siller-Jackson, Helotes, all of TX (US); Robert A. Smith, Jackson, MS (US)

(73) Assignee: Keraplast Technologies, Ltd., San Antonio, TX (US)

( * ) Notice: Subject to any disclaimer, the term of this patent is extended or adjusted under 35 U.S.C. 154(b) by 0 days.

(21) Appl. No.: 09/330,550

(22) Filed: Jun. 11, 1999

(51) Int. Cl.$^7$ .............................. A61F 13/00; A61L 15/16; A61L 15/00
(52) U.S. Cl. ................... 424/443; 424/444; 424/445; 424/446; 424/447; 424/449
(58) Field of Search .................... 424/443, 449, 424/448, 70, 74

(56) References Cited

U.S. PATENT DOCUMENTS

| | | | |
|---|---|---|---|
| 2,993,794 | 7/1961 | Moshy | 99/18 |
| 3,842,848 | 10/1974 | Karjala | 132/7 |
| 4,135,942 | 1/1979 | Kikkawa | 106/155 |
| 4,141,888 | 2/1979 | Matsuda et al. | 260/123.7 |
| 4,232,123 | 11/1980 | Braeumer et al. | 435/69 |
| 4,423,032 | 12/1983 | Abe et al. | 424/70 |
| 4,495,173 * | 1/1985 | Matsunaga et al. | 424/70 |
| 4,530,829 | 7/1985 | Abe | 424/70 |
| 4,570,629 | 2/1986 | Widra | 128/156 |
| 4,711,780 | 12/1987 | Fahim | 424/145 |
| 4,818,520 | 4/1989 | Fleischner | 424/61 |
| 4,839,168 * | 6/1989 | Abe et al. | 424/74 |
| 4,895,722 | 1/1990 | Abe et al. | 424/71 |
| 4,948,876 * | 8/1990 | Bore et al. | 530/357 |
| 4,959,213 | 9/1990 | Brod et al. | 514/21 |
| 4,983,580 * | 1/1991 | Gibson | 514/2 |
| 5,047,249 * | 9/1991 | Rothman et al. | 424/543 |
| 5,258,043 * | 11/1993 | Stone | 623/66 |
| 5,276,138 * | 1/1994 | Yamada et al. | 530/357 |
| 5,358,935 * | 10/1994 | Smith et al. | 514/21 |
| 5,487,889 * | 1/1996 | Eckert et al. | 424/93.1 |
| 5,639,448 | 6/1997 | Galleguillos et al. | 424/70.11 |
| 5,712,252 | 1/1998 | Smith | 514/21 |
| 5,763,583 * | 6/1998 | Arai et al. | 530/353 |
| 5,866,167 | 2/1999 | Van Bossuyt | 424/520 |

FOREIGN PATENT DOCUMENTS

| | | |
|---|---|---|
| 531446 * | 1/1941 | (DE) . |
| 0 454 600 | 4/1991 | (EP) . |
| 2 540 381 | 2/1983 | (FR) . |
| 2 609 393 | 2/1988 | (FR) . |
| 57-144211 | 9/1982 | (JP) . |
| 57-149211 | 9/1982 | (JP) . |
| 6-100600 * | 4/1994 | (JP) . |
| 2106154 * | 8/1996 | (RU) . |
| 2106154 | 3/1998 | (RU) . |

* cited by examiner

*Primary Examiner*—Thurman K. Page
*Assistant Examiner*—Isis Ghali
(74) *Attorney, Agent, or Firm*—Timothy S. Corder; Stephen J. Moloney; Vinson & Elkins L.L.P.

(57) ABSTRACT

A peptide derived from keratin, which can be used as a wound-healing agent. In one method for making the peptide, a keratin source such as human hair is washed, dried, and treated with an oxidizing agent such as peracetic acid for a time and temperature sufficient to swell the keratin and oxidize some of the disulfide bonds to form sulfonic acid groups. The oxidation is believed to form a series of water-soluble peptides. The oxidized hair can be filtered, and the filtrate collected and concentrated under vacuum distillation to a viscous syrup, which can be neutralized with base. The concentrate can be mixed with an excess of a water-miscible organic solvent such as methanol, and the precipitate collected and dried to form the wound-healing agent. The wound-healing agent is believed to include peptides having a molecular weight centered around 850 daltons and having at least one ionizeable group such as sulfonic acid.

17 Claims, 2 Drawing Sheets

| KERATIN PEPTIDE (μg/mL) | 0 | 0.005 | 0.01 | 0.05 | 0.1 | 0.5 | 1 | 5 | 10 | +CONTROL |
|---|---|---|---|---|---|---|---|---|---|---|
| SKIN KERATINOCYTES, DAY 5 | 0 | 6.9 | 20.24 | 17.38 | 23.07 | 28.4 | 24.94 | 24.62 | 24.4 | 28.22 |
| DERMAL FIBROBLASTS, DAY 5 | 0 | 3.95 | 5.19 | 6.36 | 6.31 | 11.26 | 9.18 | 12.36 | 11.43 | 13.48 |
| MICROVASCULAR ENDOTHELIAL CELLS, DAY 7 | 0 | -8.32 | 7.13 | 9.35 | 1.7 | 1.36 | -3.24 | 0.31 | 2.22 | 4.29 |

FIG. 2

SOLUBLE KERATIN PEPTIDE

RELATED APPLICATIONS

The present application is related to U.S. Pat. No. 5,358,935 entitled NONANTIGENIC KERATINOUS PROTEIN MATERIAL; U.S. patent application Ser. No. 09/057,161, filed Apr. 8, 1998, entitled KERATINOUS PROTEIN MATERIAL FOR WOUND HEALING APPLICATIONS AND METHOD; U.S. patent application Ser. No. 08/979,456, filed Nov. 26, 1997, entitled KERATIN-BASED HYDROGEL FOR BIOMEDICAL APPLICATIONS AND METHOD OF PRODUCTION; U.S. patent application Ser. No. 08/979,526, filed Nov. 26, 1997, entitled KERATIN-BASED SHEET MATERIAL FOR BIOMEDICAL APPLICATIONS AND METHOD OF PRODUCTION; and U.S. patent application Ser. No. 09/198,998, filed Nov. 24, 1998, entitled METHOD OF CROSSLINKING KERATIN-BASED FILMS, SHEETS AND BULK MATERIALS, entitled WATER ABSORBENT KERATIN AND GEL FORMED THEREFROM, all of which are herein incorporated by reference.

FIELD OF THE INVENTION

The present invention is related generally to water-soluble peptides. More specifically, the present invention is related to water-soluble peptides derived from keratin. In particular, the present invention is related to water-soluble peptides formed from chemically processed hair, which can be used as wound-healing agents

BACKGROUND OF THE INVENTION

Chronic wounds can be caused by a variety of events, including surgery, prolonged bedrest and traumatic injuries. Partial thickness wounds can include second degree burns, abrasions, and skin graft donor sites. Healing of these wounds can be problematic, especially in cases of diabetes mellitus or chronic immune disorders. Full thickness wounds have no skin remaining, and can be the result of trauma, diabetes (e.g., leg ulcers) and venous stasis disease, which can cause full thickness ulcers of the lower extremities. Full thickness wounds tend to heal very slowly or not at all. Proper wound care technique including the use of wound dressings is extremely important to successful chronic wound management. Chronic wounds affect an estimated four million people a year, resulting in health care costs in the billions of dollars. T. Phillips, O. Kehinde, and H. Green, "Treatment of Skin Ulcers with Cultivated Epidermal Allografts," *J. Am. Acad. Dennatol*, V. 21, pp. 191–199 (1989).

The wound-healing process involves a complex series of biological interactions at the cellular level which can be grouped into three phases: homeostasis and inflammation; granulation tissue formation and reepithelization; and remodeling. R. A. F. Clark, "Cutaneous Tissue Repair: Basic Biological Considerations," *J. Am. Acad. Dermatol*, Vol. 13, pp. 701–725 (1985). Keratinocytes (epidermal cells that manufacture and contain keratin) migrate from wound edges to cover the wound. Growth factors such as transforming growth factor-$\beta$(TGF-$\beta$) play a critical role in stimulating the migration process. The migration occurs optimally under the cover of a moist layer. Keratins have also been found to be necessary for reepithelization. Specifically, keratin types K5 and K14 have been found in the lower, generating, epidermal cells, and types K1 and K10 have been found in the upper, differentiated cells. I. K. Cohen, R. F. Diegleman, and W. J. Lindblad, eds., *Wound Healing: Biochemical and Clinical Aspects*, W. W. Saunders Company, 1992. Keratin types K6 and K10 are believed to be present in healing wounds, but not in normal skin. Keratins are major structural proteins of all epithelial cell types and appear to play a major role in wound healing.

An optimum wound dressing would protect the injured tissue, maintain a moist environment, be water permeable, maintain microbial control, deliver healing agents to the wound site, be easy to apply, not require frequent changes and be non-toxic and non-antigenic. Although not ideal for chronic wounds, several wound dressings are currently on the market, including occlusive dressings, non-adherent dressings, absorbent dressings, and dressings in the form of sheets, foams, powders and gels. S. Thomas, *Wound Management and Dressing*, The Pharmaceutical Press, London, 1990.

Attempts have been made to provide improved dressings that would assist in the wound-healing process using biological materials such as growth factors. These biologicals have proven very costly and, due to the lack of an appropriate delivery vehicle, have shown minimal clinical relevance in accelerating the chronic wound-healing process relative to their cost. In cases of severe full thickness wounds, autografts (skin grafts from the patient's body) are often used. Although the graft is non-antigenic, it must be harvested from a donor site on the patient's body, creating an additional wound. In addition, availability of autologous tissue may not be adequate. Allografts (skin grafts from donors other than the patient) are also used when donor sites are not an option. Allografts essentially provide a "wound dressing" that provides a moist, water-permeable layer, but are rejected by the patient, usually within two weeks, and do not become part of the new epidermis.

What would be advantageous is a non-toxic, non-antigenic, inexpensive wound-healing agent having the ability to accelerate the rate of wound healing and allow non-healing wounds to heal.

SUMMARY OF THE INVENTION

A water-soluble peptide derived from a keratinous source such as hair and methods for making same are provided. One method includes providing a keratinous material having disulfide linkages and oxidizing the keratinous material with an oxidizing agent, such that some disulfide linkages are cleaved and oxidized, forming water-soluble peptides. The water-soluble peptides can be separated, collected, dried, and used as a wound-healing agent. A preferred source of keratinous material is hair, such as human hair.

In one method, hair is oxidized with a sufficient concentration of oxidizing agent for a sufficient time and temperature so as to cleave a significant portion of the hair disulfide bonds, such that some disulfide bonds are oxidized to form hydrophilic groups such as sulfonic acid and such that water-soluble peptides are produced. Examples of oxidizing agents include, but are not limited to, hydrogen peroxide, peracetic acid, percarbonates, persulfates, chlorine dioxide, sodium and calcium peroxides, perborates, and hypochlorite. The oxidized hair can be filtered, the filtrate collected, and neutralized with base. Water soluble peptides from the neutralized filtrate can be precipitated from solution by mixing the filtrate with a water-miscible organic solvent such as methanol. The precipitate can be collected using centrifugation and the collected filtrate dried. In one method, about 20 percent of the original hair mass is collected as peptide material after drying. The dried precipitate can be ground into a fine powder.

Peptides produced according to the present invention are largely water soluble and have an average molecular weight of about 850 daltons and an average chain length of about 10 amino acids. The peptide chains are believed to have attached a hydrophilic group, for example, an ionizable group such as sulfonic acid. In particular, most peptides are believed to have at least one sulfonic acid group formed from the oxidization of disulfide linkages of hair. One product made according to the present invention is a powder that is whitish to yellow in color and readily soluble in water.

In use, the peptide powder can be placed over a wound as a powder. The peptide powder can also be formulated into any water-based solution, cream, gel, or other vehicle for convenient application to a wound. In addition, a peptide solution could be incorporated into or cast onto a polymer wound dressing or a keratin wound dressing sheet for application to a wound. In in vitro trials, the peptide wound-healing agent was shown to enhance proliferation of human skin keratinocytes, human dermal fibroblasts, and microvascular endothelial cells. Applicants believe that the peptide fraction isolated according to the present invention is a highly active form of a wound-healing agent.

BRIEF DESCRIPTION OF THE DRAWINGS

FIG. 2 is a table of experimental results illustrating proliferation of cells critical to the wound-healing process after application of a keratin peptide wound-healing agent made according to the present invention.

DETAILED DESCRIPTION OF THE INVENTION

Figure 1:
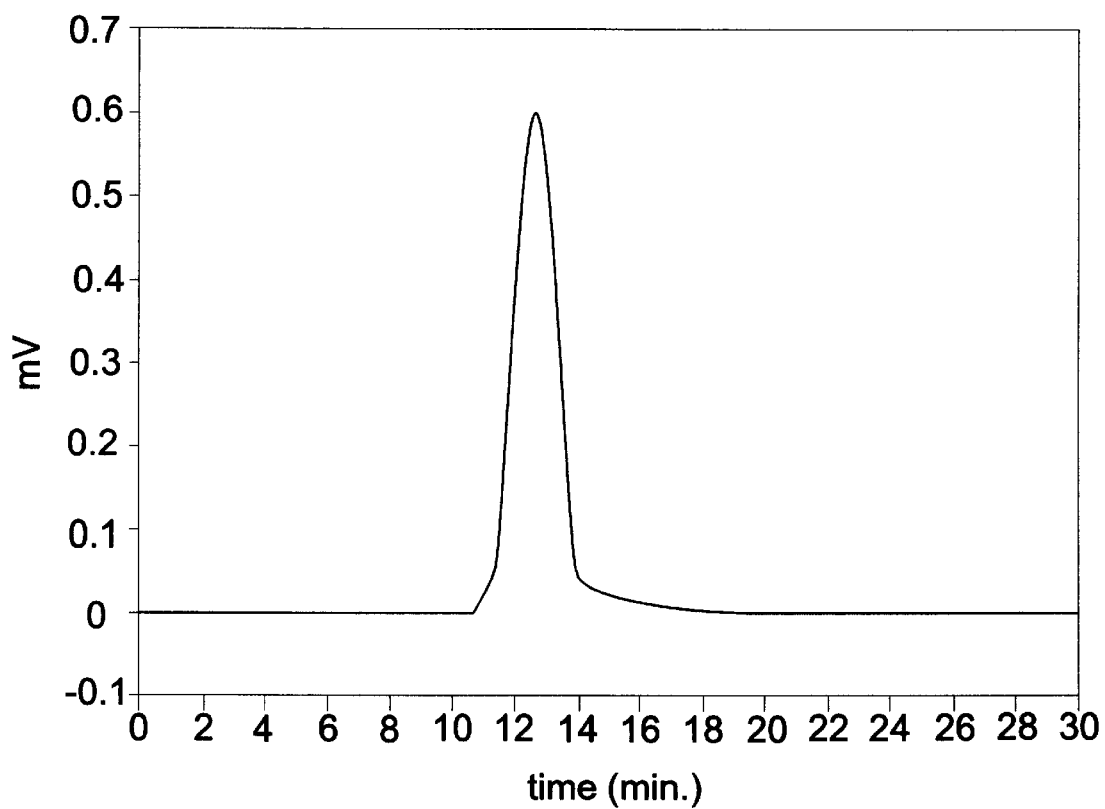
FIG. 1 is a chromatogram showing the molecular weight distribution of one sample of the soluble peptide made according to the present invention.

The present invention provides a wound-healing agent which can include a peptide having an ionizable pendant group such as sulfonic acid which can be derived from an oxidized protein disulfide linkage. A preferred source of protein is keratin. One preferred source of keratin is hair. While hair is a preferred source of keratinous material, other keratinous materials such as animal hair, skin, beaks, hooves, feathers, and nails are also suitable for use in the present invention. The patient or a human donor are some preferred sources of hair, as hair from these sources is most likely to result in a non-antigenic wound-healing product, although animal hair may be acceptable for many individuals. In one method according to the present invention, hair is provided, preferably clean and unbleached. In another method, the hair is washed with Versa-Clean TM (Fisher Scientific, Pittsburgh, Pa.), rinsed with deionized water, and dried.

The hair can be oxidized in peracetic acid or another suitable reagent such as $H_2O_2$. One method utilizes between about 1% to 32% peracetic acid, at a temperature between about 0 degrees C and 100 degrees C for between 0.5 and 24 hours. One method treats 30 grams of hair with 500 mL of 4 volume percent peracetic acid at 4 degrees C for 24 hours. Another method treats the hair at room temperature for 24 hours. Yet another method treats the hair at about 90 degrees C for about 10 hours. In a preferred method, the hair is treated by boiling the hair in the oxidizing agent for at least about 2 hours, and preferably for about 5 hours. The higher oxidizing temperature is believed to produce higher yields relative to the lower oxidizing temperature. In various embodiments, at least 5, 10, and 15 weight percent of the original hair weight is eventually recovered as peptides by application of sufficient oxidant, heat, and time. In one embodiment, about 20 weight percent of the original hair can be eventually recovered as peptides, useful for the present invention. The treatment with oxidizing agent is believed to open the cuticle structure of the hair and to swell the keratin. Treatment with oxidizing agent (e.g., $H_2O_2$ and peracetic acid) is believed to at least partially oxidize the naturally occurring disulfide linkages to produce a protein with cysteic acid side groups ($—CH_2SO_3H$), which are also referred to as sulfonic acid groups in the present application. The treatment with oxidizing agent is not believed to break a substantial portion of peptide backbone bonds. The result is believed to include short-chain peptides that have at least one ionizable pendant group such as sulfonic acid, where the peptides are soluble in water at physiological pH. In general, the present invention includes the production of water-soluble peptides from a keratinous material including peptides having hydrophilic groups such as sulfonic acid groups.

The oxidized hair can be recovered, for example with filtration through a coarse fritted glass filter, and the filtrate collected. Filtration thus separates the water-soluble peptides from the remaining keratin source such as hair, allowing collection of the water-soluble peptides in the filtrate. While filtration is a preferred separation method, other suitable separation methods such as decantation or dialysis are also within the scope of the invention. The hair can be rinsed numerous times with deionized water to increase the amount of soluble protein that is washed off the hair. The hair can be discarded or kept for other uses. The filtrate in one embodiment is concentrated about ten-fold using vacuum distillation, leaving a viscous syrup. In one method, the filtrate is concentrated until the concentrated filtrate contains about 120 grams of peptide per liter. One vacuum distillation method uses between about 5 and 10 mm Hg pressure at a pot temperature of about 40 degrees C. In some methods, concentration is performed at a later stage of the process.

The filtrate can be neutralized using a base. The filtrate is neutralized to facilitate the precipitation of the peptides. In one method, 3 to 4 normal ammonium hydroxide is used as a base in the amount of about 0.1 mL to 1 mL of the viscous syrup formed from concentrating the filtrate. In another method, about 1 mL of base is added to 100 mL of unconcentrated filtrate. The base can be added until the pH is about 7.

Neutralized filtrate can then be mixed with a water-miscible organic solvent such as methanol, ethanol, acetone, or tetrahydrofuin. In one embodiment, about 6 to 10 mL of methanol is added to 1 mL of the viscous syrup containing the concentrated filtrate. In another embodiment, about 60 to 100 mL of methanol is added to 1 mL of the unconcentrated filtrate. The water-soluble peptide has lower solubility in the organic solvent/water mixture and cleanly precipitates out.

The precipitate can then be collected using well known methods such as centrifugation, filtration, or decanting. The precipitate can then be dried using evaporation, preferably without the application of heat. In one method, the precipitate is dried at room temperature. In another method, the precipitate is dried under vacuum, again without the application of heat. No grinding is required, as the precipitate obtained, when dry, is already a powder. In some embodiments, the dried precipitate is further processed by grinding into a fine powder using a mortar and pestle or equivalent grinding instrument.

The powder obtained from one method is whitish to yellow in color and is completely soluble in water. Analysis of these samples have shown them to be Gaussian distributions of low molecular weight peptides, as shown in the chromatogram of FIG. 1. Elemental analysis has shown the carbon content to be between 38.39 and 41.59 weight percent; the hydrogen content to be between 5.74 and 6.16 weight percent; the nitrogen content to be between 15.19 and 15.89 weight percent; the oxygen content to be between 23.67 and 26.97 weight percent; and the sulfur content to be between 3.80 and 4.78 weight percent. Analysis of mass spectra shows a distribution of molecular weight species, centered at approximately 850 daltons.

The peptide provided by the present invention can be used in several applications. The skin healing properties of the peptide can be used to promote healing, repair, and cell growth in keratinous tissue generally. The peptide can be used to treat damaged skin and skin wounds including, for example, rashes, including diaper rash, burns including sunburn, cuts, abrasions, punctures, sores including bed sores, ulcers including diabetic ulcers and other skin injuries or irritations. The peptide can also be used to treat aging, weakened or damaged skin, including, for example, wrinkled skin. In one use, the keratinous tissue is damaged tissue located either externally or internally. In one example of use, an external wound can be treated by applying the peptide to the wound. In one method, the peptide is admixed with a cream, lotion, or gel before application to the skin. In another method, the peptide is added to a keratin hydrogel prior to application to the skin. A keratin hydrogel can be made according to, for example, U.S. patent application Ser. No. 08/979,456, filed Nov. 26, 1997, entitled KERATIN-BASED HYDROGEL FOR BIOMEDICAL APPLICATIONS AND METHOD OF PRODUCTION. In another method, the peptide can be added to a wound dressing prior to application. For example, the peptide can be added to a keratin sheet as described in U.S. patent application Ser. No. 08/979,526, filed Nov. 26, 1997, ENTITLED KERATIN-BASED SHEET MATERIAL FOR BIOMEDICAL APPLICATIONS AND METHOD OF PRODUCTION. In another use of the invention, the peptide can be applied internally to damaged keratinous tissue lining the GI tract by orally administering the peptide. Examples of such damage can result from ulcers, colitis, or Crohn's disease.

The peptide can also be added as a cell growth stimulant to a tissue engineering scaffold such as the sheet described in U.S. patent application Ser. No. 09/198,998, filed Nov. 24, 1998, entitled METHOD OF CROSS-LIN KGN KERATIN-BASED FILMS, SHEETS, AND BULK MATERIALS. The peptide is believed suitable to speed repair of sun or weather damaged skin. The peptide can be mixed with a carrier lotion such as lanolin and applied to the skin. The peptide can also be added to cosmetics to impart a skin healing property to the cosmetic. Cosmetic bases are believed suitable for inclusion of peptides made according to the present invention.

EXPERIMENTAL RESULTS

Referring now to the table in FIG. 2, cell studies were performed on human skin keratinocytes, human dermal fibroblasts, and microvascular endothelial cells, as indicated, to determine the effect of the keratin peptide on proliferation of cells critical to the wound-healing process. Known growth factors for each cell line were used as positive controls. The following concentrations of keratin peptide were used: 0 (control, media alone); 0.005; 0.01; 0.05; 0.1; 0.5; 1; 5; and 10 micrograms per milliliter. At day 5 of the study, the cells were analyzed using a technique that counts the number of cells. The purpose of this study was to assess cell proliferation as a result of their exposure to the keratin peptide, relative to no exposure (media alone) and to known stimulants for each cell type, the "positive control." Exposure to media alone was considered the baseline of the study, so the average number of cells in the baseline cultures was subtracted out of the average number of cells in the cultures containing the soluble peptides and the positive control for each cell line. This process mathematically reduces the baseline to zero and everying else becomes relative to zero, as seen in the first column of data. These subtracted numbers are divided through by the average baseline value and become a percent above or below baseline. The numbers in the table represent the percent above baseline.

As can be seen from inspection of FIG. 2, the keratin-derived peptide stimulated growth of the selected cell lines and compares favorably with the known growth factors for each cell line. In particular, at 0.5 micrograms per milliliter of peptide, skin keratinocytes grew over 28% percent more than with media alone, and at 5 micrograms peptide per milliliter, dermal fibroblasts grew over 12 percent more relative to the baseline. At 0.05 micrograms of peptide per milliliter of media, microvascular endothelial cells grew more than 9 percent more than the media only baseline. Application of the keratin-derived peptide is thus believed to be usefull as a wound-healing agent.

Numerous advantages of the invention covered by this document have been set forth in the foregoing description. It will be understood, however, that this disclosure is, in many respects, only illustrative. Changes may be made in details, particularly in matters of reagents, concentrations, and step order, without exceeding the scope of the invention. The inventions's scope is, of course, defined in the language in which the appended claims are expressed.

What is claimed is:

1. A method for obtaining water soluble peptides from a keratin-containing material such as human or animal hair, fur, hooves, feathers, or human or animal nails, said method comprising:

oxidizing said keratin-containing material in an aqueous solution;

filtering said oxidized aqueous solution to obtain a water soluble portion;

neutralizing said water soluble portion; and adding a water-miscible organic solvent to said water soluble portion, such that a precipitate is formed;

wherein said precipitate comprises water soluble peptides.

2. The method of claim 1, further comprising drying said precipitate to obtain a powder.

3. The method of claim 1, wherein said oxidizing includes suspending said keratin-containing material in a solution comprising an oxidizing agent selected from hydrogen peroxide, peracetic acid, a percarbonate, a persulfate, chlorine dioxide, sodium peroxide, calcium peroxide, a perborate, or hypochlorite.

4. The method of claim 1, wherein said oxidizing includes suspending said keratin-containing material in a solution comprising from about 1 to about 32 volume percent peracetic acid or hydrogen peroxide.

5. The method of claim 1, wherein said method includes oxidizing said keratin-containing material at a temperature of from about 0° C. to about 100° C. for a period of from about one-half to about 24 hours.

6. The method of claim 1, wherein said method includes oxidizing said keratin-containing material at a temperature of about 4° C. for about 24 hours.

7. The method of claim 1, wherein said method includes oxidizing said keratin-containing material at room temperature for about 24 hours.

8. The method of claim 1, wherein said method includes oxidizing said keratin-containing material at about 90° C. for about 10 hours.

9. The method of claim 1, wherein said oxidizing includes boiling said aqueous solution for from about one-half to about 6 hours.

10. The method of claim 1, wherein said oxidizing is effective to release up to about 20% of the weight of the keratin-containing material as soluble peptides.

11. The method of claim 1, wherein said water-miscible organic solvent is methanol, ethanol, acetone, tetrahydrofuran or a combination thereof.

12. The method of claim 1, wherein said water-miscible organic solvent is methanol.

13. The method of claim 1, wherein said water-miscible organic solvent is ethanol.

14. The method of claim 1, wherein said water soluble portion is concentrated up to about 10 fold prior to adding said water-miscible organic solvent.

15. The method of claim 1, wherein said water-miscible organic solvent is added at a volume ratio of organic solvent to aqueous solution of from about 60:1 to about 100:1.

16. The method of claim 14, wherein said water-miscible organic solvent is added at a volume ratio of organic solvent to aqueous solution of from about 6:1 to about 10:1.

17. The method of claim 1, wherein said keratin-containing material is human hair.

* * * * *